US011071588B2

(12) United States Patent
Negus et al.

(10) Patent No.: US 11,071,588 B2
(45) Date of Patent: Jul. 27, 2021

(54) LASER TREATMENT OF WOUNDS

(71) Applicant: Sciton, Inc., Palo Alto, CA (US)

(72) Inventors: Daniel K. Negus, Palo Alto, CA (US); James L. Hobart, Palo Alto, CA (US); Craig Fortier, Palo Alto, CA (US); Sha Tong, Palo Alto, CA (US); Chris Rasmussen, Palo Alto, CA (US)

(73) Assignee: Sciton, Inc., Palo Alto, CA (US)

( * ) Notice: Subject to any disclaimer, the term of this patent is extended or adjusted under 35 U.S.C. 154(b) by 31 days.

(21) Appl. No.: 16/465,591

(22) PCT Filed: Dec. 6, 2017

(86) PCT No.: PCT/US2017/064805
§ 371 (c)(1),
(2) Date: May 31, 2019

(87) PCT Pub. No.: WO2018/106751
PCT Pub. Date: Jun. 14, 2018

(65) Prior Publication Data
US 2019/0380779 A1      Dec. 19, 2019

Related U.S. Application Data

(60) Provisional application No. 62/431,078, filed on Dec. 7, 2016.

(51) Int. Cl.
*A61B 18/20* (2006.01)
*A61B 18/00* (2006.01)
(Continued)

(52) U.S. Cl.
CPC .. *A61B 18/203* (2013.01); *A61B 2018/00577* (2013.01); *A61B 2018/00589* (2013.01);
(Continued)

(58) Field of Classification Search
None
See application file for complete search history.

(56) References Cited

U.S. PATENT DOCUMENTS

| 2014/0074068 A1* | 3/2014 | Olmstead | A61B 5/0066 |
| | | | 604/522 |
| 2014/0276201 A1* | 9/2014 | Woloszko | A61B 5/14546 |
| | | | 600/562 |
| 2015/0202007 A1* | 7/2015 | Manstein | A61B 18/203 |
| | | | 606/9 |

OTHER PUBLICATIONS

International Search Report and Written Opinion corresponding to PCT/US2017/064805, dated Feb. 15, 2018, 9 pages.
(Continued)

*Primary Examiner* — Brian T Gedeon
(74) *Attorney, Agent, or Firm* — E. Eric Mills; Nexsen Pruet, PLLC

(57) ABSTRACT

In one aspect, methods of treating a wound are described herein. A method described herein, in some embodiments, comprises treating a wound, such as a chronic wound, by performing a full field laser ablation in a wound bed of the wound and subsequently performing a fractional laser ablation in the wound bed. Additionally, in some cases, the fractional laser ablation step is carried out at substantially the same time as, or immediately following, the full field laser ablation step. In addition, in some instances, a method described herein further comprises performing debridement in the wound bed prior to performing the full field laser ablation in the wound bed.

20 Claims, 4 Drawing Sheets

(51) Int. Cl.
    *A61N 5/06*     (2006.01)
    *A61N 5/067*    (2006.01)
(52) U.S. Cl.
    CPC ............... *A61B 2018/00625* (2013.01); *A61B 2018/20359* (2017.05); *A61N 5/0624* (2013.01); *A61N 2005/067* (2013.01); *A61N 2005/0642* (2013.01); *A61N 2005/0661* (2013.01)

(56) References Cited

OTHER PUBLICATIONS

Sciton, Contour TRL with MicroLaserPeel & ProFractional Therapy: Complete Resurfacing Solutions from Sciton; The Sciton Edge, 2014, 2600-029-08, Rev. E, p. 1 of 4, Left Column, Specifications Table; p. 2 of 4—Left Column; p. 3 of 4, Right Column; p. 4 of 4, Left Column; p. 4 of 4—Bottom Section.

Bowen, R, MD, Periorbital Rejuvenation with the Contour TRL and ProFractionai-XC Laser Devices, West Virgina University—East, The Center for Positive Aging, Marinsburg, WV, Sciton, 2010, 2600-003-06.

Bazarov, I, et al., Laser Debridement: Can It Have an Impact for Chronic Wounds?, Podiatry Today, Apr. 22, 2014, vol. 27, No. 5, pp. 50-56; p. 3 of 14, Third Paragraph; p. 6 of 14, First Parapgraph; p. 6 of 14, Fourth Paragraph.

\* cited by examiner

LASER TREATMENT OF WOUNDS

CROSS REFERENCE TO RELATED APPLICATIONS

This application is a U.S. National Phase of PCT/US2017/064805, filed Dec. 6, 2017, which claims priority pursuant to 35 U.S.C. § 119 to U.S. Provisional Patent Application No. 62/431,078, filed on Dec. 7, 2016, which are incorporated by reference herein in its their entireties.

FIELD

This invention relates to systems and methods for the treatment of wounds and, in particular, to systems, devices, and methods for treating chronic wounds with lasers.

BACKGROUND

Many wounds, including chronic wounds, are not easily healed by "normal" wound treatment methods, such as cleaning of the wound, treatment with antibiotics, and/or reliance on the patient's or host's own immune system response. Additionally, some wounds associated with an underlying condition or disease, such as diabetic ulcers, resist healing even upon treatment of the underlying condition or disease. Such chronic wounds frequently lead to chronic infection and amputation, as well as other challenges such as pain, discomfort, and malodor. Accordingly, there is a need for improved methods systems, and devices for the treatment of wounds, particularly chronic wounds.

SUMMARY

In one aspect, methods of treating a wound are described herein which, in some cases, can provide one or more advantages compared to some other methods. For example, in some embodiments, a method described herein can provide more complete and rapid healing of a wound, including a chronic wound. Additionally, a method described herein can prevent Or reduce chronic infection and/or eliminate the need to amputate a wounded body party. A method described herein can also reduce the pain, discomfort, and malodor associated with a wound. Moreover, a method described herein can treat a wound more efficiently and cost-effectively, compared to some other methods.

A method described herein, in some embodiments, comprises treating a wound, such as a chronic wound, by performing a full field laser ablation in a wound bed of the wound and subsequently performing a fractional laser ablation in the wound bed. Additionally, in some eases, the fractional laser ablation step is carried out at substantially the same time as, or immediately following, the full field laser ablation step. For example, in some instances, the fractional laser ablation is begun 10 minutes or less after the full field laser ablation is ended. Moreover, in some cases, the full field laser ablation removes at least 90% of biofilm and/or necrotic tissue present in the wound bed immediately prior to the full field laser ablation. Further, in some instances, the full field laser ablation and/or the fractional laser ablation of a method described herein, is carried out using a laser scanner and/or using a laser having an erbium-doped yttrium aluminum garnet lasing medium (an Er:YAG laser).

In addition, in some embodiments, a method described herein further comprises performing debridement in the wound bed prior to performing the full field laser ablation in the wound bed. Such "pre-treatment" debridement, in some cases, can be sharp debridement.

Moreover, in some cases, a method described herein also comprises carrying out one or more additional wound treatment steps following completion of treatment steps mentioned above. For example, in some embodiments, a method described herein further comprises carrying out one or more additional wound treatment steps following debridement, full field laser ablation, and fractional laser ablation. Such additional treatments can include applying an antibiotic to the wound, desiccating, the wound, and/or irradiating the wound with ultraviolet (UV) light.

It should be further noted that methods described herein can also be used to treat damaged tissue that may or may not constitute a "wound" per se. For example, in some cases, a method described herein comprises treating a damaged tissue site other than a wound by performing a full field laser ablation in, at, or on a non-wound damaged tissue site and subsequently performing a fractional laser ablation in, at, or on the non-wound damaged tissue site.

In another aspect, systems or devices for treating a wound (or non-wound damaged tissue site) are described herein. In some embodiments, such a system or device comprises a laser configured to selectively perform full field laser ablation and fractional laser ablation on a wound (or other damaged tissue site) of the same patient, including in an alternating or sequential manner. In some such instances, the laser is configured to perform fractional laser ablation on the wound (or other damaged tissue site) after the laser performs full field laser ablation on the wound (or other damaged tissue site). Moreover, in some cases, a system or device described herein comprises a plurality of lasers rather than a single laser. For instance, in some embodiments, a system or device comprises a first laser configured to perform full field laser ablation and a second laser configured to perform fractional laser ablation. Additionally, in some cases, the first laser and the second laser are configured to perform full field laser ablation and fractional laser ablation, respectively, on a wound or other damaged tissue site) of the same patient sequentially. In particular, in some instances, the second laser is configured to perform fractional laser ablation on the wound (or other damaged tissue site) after the first laser performs full field laser ablation on the wound (or other damaged tissue site). Moreover, in some embodiments, the laser (or the first laser and/or the second laser) of a system or device described herein comprises a laser scanner and/or an Er:YAG laser.

These and other embodiments are described in more detail in the detailed description which follows.

DETAILED DESCRIPTION

Figure 1:
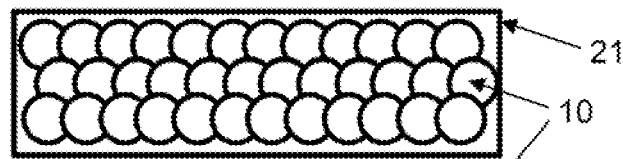
FIG. 1 schematically illustrates a full field laser ablation process according to one embodiment described herein.

Embodiments described herein can be understood more readily by reference to the following detailed description, examples, and figures. Elements, apparatus, and methods described herein, however, are not limited to the specific embodiments presented in the detailed description, examples, and figures. It should be recognized that these embodiments are merely illustrative of the principles of the present invention. Numerous modifications and adaptations will be readily apparent to those of skill in the art without departing from the spirit and scope of the invention.

In addition, all ranges disclosed herein are to be understood to encompass any and all subranges subsumed therein. For example, a stated range of "1.0 to 10.0" should be considered to include any and all subranges beginning with a minimum value of 1.0 or more and ending with a maximum value of 10.0 or less, e.g., 1.0 to 5.3, or 4.7 to 10.0, or 3.6 to 7.9. Similarly, a stated range of "1 to 10" should he considered to include any and all subranges beginning with a minimum value of 1 or more and ending with a maximum value of 10 or less. e.g., 1 to 5, or 4 to 10, or 3 to 7, or 5 to 8.

All ranges disclosed herein are also to be considered to include the end points of the range, unless expressly stated otherwise. For example, a range of "between 5 and 10" or "from 5 to 10" or "5-10" should generally be considered to include the end points 5 and 10.

Further, when the phrase "up to" is used in connection with an amount or quantity, it is to be understood that the amount is at least a detectable amount or quantity. For example, a material present in an amount "up to" a specified amount can be present from a detectable amount and up to and including the specified amount.

1. Methods of Treating a Wound

In one aspect, methods of treating a wound are described herein. As stated above, a method described herein, in some embodiments, comprises treating a wound, such as a chronic wound, by performing a full field laser ablation in a wound bed of the wound and subsequently performing a fractional laser ablation in the wound bed. In some cases, the fractional laser ablation step is carried out at substantially the same time as, or immediately following, the full field laser ablation step. In addition, in some instances a method described herein further comprises performing debridement in the wound bed prior to performing the full field laser ablation in the wound bed. Moreover, in some cases, a method described herein further comprises carrying out one or more additional treatments in the wound bed following debridement, full field laser ablation, and/or fractional laser ablation steps described herein.

Many wounds, including chronic wounds, exhibit an accumulation of slough (consisting of various proteins such as fibrin) and exudate, as well as exhibiting particularly a microbial biofilm. Such a biofilm generally includes a large number of microorganism cells adhered to one another and to a substrate. Additionally, in some cases, the adhered cells are embedded within an extracellular polymeric substance ("EPS," also known as "slime") produced by the microorganisms.

Not intending to be bound by theory, it is believed that methods described herein can dramatically improve wound healing, especially chronic wound healing, by hindering or destroying the ability of biofilm present in a wound bed from reforming and/or otherwise limiting the effectiveness of antibiotic treatments, other treatments, host immune responses to the wound, in wound treatment, particularly chronic wound treatment, all or substantially all slough, slime, necrosis, and the like are generally removed from a wound via scissors, curette, and wiping to the greatest extent possible without traumatizing the wound bed. Unfortunately, even with thorough scraping, wiping, and other such treatments, some amount of biofilm typically remains in a chronic wound bed. Such "residual" biofilm comprises biofilm components that do not necessarily form a mature or complete biofilm but that once were part of a mature or complete biofilm. Moreover, this residual biofilm can typically reform into mature biofilm in as little as 24-36 hours. Again not intending to be bound by theory, it is believed that methods of treating a wound described herein can destroy such residual biofilm and/or hinder the ability of residual biofilm to reform quickly, thereby improving the effectiveness of antibiotics, other treatment modalities, and/or the host immune response in healing the wound. Thus, in some embodiments, a method described herein can "reset" the wound microbiota and the wound bed surface.

Turning now to specific steps of methods, methods described herein comprise performing a full field laser ablation. As understood by one of ordinary skill in the art, "full field" laser ablation refers to a laser ablation process in which laser interaction with tissue corresponds to 100% or substantially all of a targeted area being treated (e.g., a wound bed) by irradiation with an ablating laser beam, where an "ablating" laser beam is understood to refer to a laser beam of sufficient peak power to ablate, vaporize, destroy, and/or remove biological tissue irradiated by the laser beam. In some cases, the ablating laser beam (which may have a spot size, for example, of about 4 mm) covers or "scans" all or substantially all of the targeted area with an overlapping serpentine pattern of "passes" of the laser beam or spot. For instance, in some embodiments, the ablating laser beam covers or scans at least 90%, at least 95%, at least 98%, or at least 99% of the targeted area (e.g., the wound bed of the wound being treated). In some cases, the ablating laser beam coves or scans 100% of the targeted area. It is further to be understood that full field laser ablation can be carried out with a variety of spot sizes, scan or exposure patterns, and lasers. In general, a full field laser ablation step described herein can be carried out in any manner not inconsistent with the objectives of the present disclosure.

Figure 2:
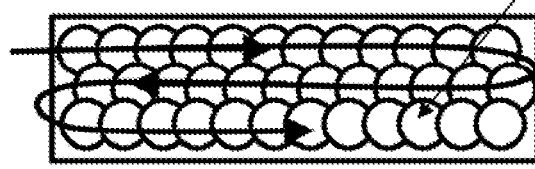
FIG. 2 schematically illustrates a hill field laser ablation process according to one embodiment described herein.
Figure 3:
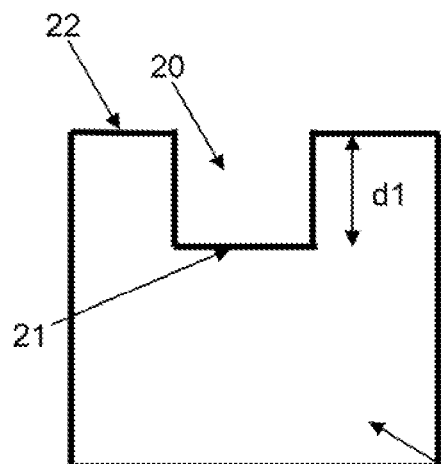
FIG. 3 schematically illustrates a sectional view of a wound following a full field laser ablation process according to one embodiment described herein.
Figure 4:
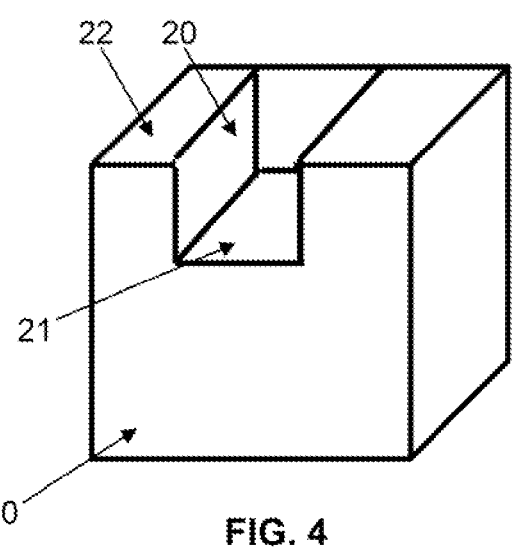
FIG. 4 schematically illustrates a perspective view of the wound of FIG. 3.

An exemplary full field laser ablation process is illustrated in FIGS. 1-4. Specifically, FIG. 1 and FIG. 2 schematically illustrate a top or plan view of a scan or pattern of laser beam spots (10) during the course of carrying out a full field laser ablation according to one embodiment described herein. As further illustrated in FIG. 3 and FIG. 4, the spots (10) cover an exterior surface (21) of a wound bed (20) of a host or patient (30). With reference once more to FIG. 1 and FIG. 2, the spots (10) overlap as the ablating laser beam (represented by spots (10)) traverses the surface (21) in a serpentine pattern, as indicated by the directional arrows overlaid on the spots (10) in FIG. 2. As the ablating laser beam traverses the surface (21), tissue and/or other material forming the surface (21) are ablated, vaporized, destroyed, or otherwise removed from the wound bed (20), causing the surface (21) to be "lowered" in a depth direction perpendicular to the surface (21) and perpendicular to an adjacent, non-treated surface (22) of the patient or host (30). As specifically illustrated in FIG. 1 and FIG. 2, the ablating laser beam performs three back and forth "passes" in the wound bed (20). However, it is to be understood that any desired number of passes can be performed to cover the entire surface (21). Similarly, the entire surface (21) can be traversed as many times as needed to "lower" the surface (21) to a desired depth beneath the original surface of the wound bed or beneath the adjacent non-treated surface (22). It is further to be understood that each pass of the ablating laser beam ablates, vaporizes, destroys, or removes tissue (such as necrotic tissue) from the wound bed, such that the depth of full field laser ablation corresponds to a depth of tissue ablated, vaporized, destroyed, or removed. As illustrated in FIG. 3, the depth of full field laser ablation is "d1." It should be noted that FIG. 3 illustrates a sectional view of the wound bed (20) after completion of the full field laser ablation to depth d1, while FIG. 4 illustrates a perspective view of the same wound bed (20) after completion of the full field laser ablation to depth d1.

The depth of ablation in a full field laser ablation step can vary. Any depth not inconsistent with the objectives of the present disclosure may be used. For example, in some embodiments, the full field laser ablation step removes at least 90%, at least 95%, at least 98%, or at least 99% of necrotic tissue in the wound bed to a depth of up to 1000 µm or to a depth of up to 2000 µm. In some eases, the full field laser ablation step removes at least 90%, at least 95%, at least 98%, or at least 99% of tissue in the wound bed to a depth of 50-2000 µm, 50-1000 µm, 50-500 µm, 50-300 µm, 50-200 µm, 100-2000 µm, 100-1000 µm, 100-500 µm, 100-300 µm, 100-200 µm, 200-2000 µm, 200-1000 µm, 200-500 µm, 400-2000 µm, 400-1000 µm, 500-2000 µm, 500-1000 µm, or 1000-2000 µm.

Additionally, in some embodiments, a full field laser ablation step of a method described herein removes or disrupts all or substantially all of various undesired components within a wound bed. In certain preferred embodiments, for example, a full field laser ablation step removes at least 90% of biofilm and/or necrotic tissue present in the wound bed immediately prior to the full field laser ablation, where "removing" biofilm and/or necrotic tissue includes ablating, vaporizing, destroying, and otherwise removing the biofilm and/or necrotic tissue. In some cases, a full field laser ablation step removes at least 95%, at least 98%, or at least 99% of biofilm and or necrotic tissue present in the wound bed immediately prior to the full field laser ablation. In some instances, a full field laser ablation step removes 90-100%, 90-99%, 90-95%, 95-100%, 95-99%, or 98-100% of biofilm and/or necrotic tissue present in the wound bed immediately prior to the full field laser ablation. Not intending to be bound by theory, it believed that removing biofilm and/or necrotic tissue in this manner can facilitate and/or improve the effectiveness of subsequent stimulation of host wound-healing and/or immune responses, such as through fractional laser ablation.

The spot size aa full field laser ablation step may also vary. Any spot size not inconsistent with the objectives of the present disclosure may be used. In some cases, for instance, the spot size is 0.5-10 mm, 0.5-5 mm, 1-10 mm, or 1-5 mm. Other spot sizes may also be used.

Moreover, a laser or laser beam used for a full field laser ablation step described herein can have any power and any peak or average emission wavelength not inconsistent with the objectives of the present disclosure. For example, in some embodiments, a laser or laser beam used for full field laser ablation has a peak or average emission wavelength in the infrared (IR) region of the electromagnetic spectrum. In some such cases, a laser or laser beam used for full field laser ablation has a peak or average emission wavelength in the range of 1-4 µm, 1-3 µm, 2-4 µm, 2-3 µm, 8-12 µm, or 9-11 µm. For example, in some embodiments, the full field laser ablation is preferably carried out using an Er:YAG laser or laser beam, including a neodymium-doped Er:YAG laser or laser beam having a peak or average emission wavelength of 2940 mm. In other cases, the full field laser ablation is carried out using a carbon dioxide laser or laser beam. Further, in some instances, a laser or laser beam used for full field laser ablation has an average power of 5 to 200 W.

Additionally, in some preferred embodiments, a full field laser ablation is carried out using a laser scanner. A "laser scanner," for reference purposes herein, refers to an apparatus which can be attached to a laser system for delivery of a laser beam over an area defined by the operator and assisted by a computer control system which is larger than a single spot of the laser beam. A typical construction of this apparatus involves an opto-mechanical arrangement of two orthogonal motors with mirrors mounted on them which receive the laser beam and are controlled by a computer control system. Each motor or actuator is capable of directing the beam in an axis. The combination of two orthogonal motors/mirrors allows the scanner to draw any arbitrary pattern in two dimensions (e.g., x and y) on the tissue or other targeted area.

It is further to be understood that a full field laser ablation step described herein can be carried out using any laser system not inconsistent with the objectives of the present disclosure. Such a system may, for instance, include a laser operable to produce a laser beam having characteristics described hereinabove, as well as one or more lenses, mirrors, actuators, or other hardware or software for directing the laser beam to a desired location on a patient and/or within a wound bed. One exemplary system is described further hereinbelow in Section II.

Methods described herein also comprise performing a fractional laser ablation. "Fractional" laser ablation or coagulation, as understood by one of ordinary skill in the art refers to a laser ablation or coagulation process in which an ablating or coagulating laser beam is used to selectively ablate, coagulate, vaporize, destroy, or remove columns of tissue, or "drill holes," in a targeted area such as a wound bed. Further, such coagulated columns or columnar vacancies or "holes" formed by fractional laser ablation can define a pattern or array of columns or vacancies or holes in the targeted area, where the columns or vacancies or holes have a desired diameter, depth, and areal density (of less than 100%) on a surface of the wound bed. Fractional laser ablation can be carried out with a variety of spot sizes, scan or exposure patterns, and lasers. In general, a fractional laser ablation step described herein can be carried out in any manner not inconsistent with the objectives of the present disclosure.

Figure 5:
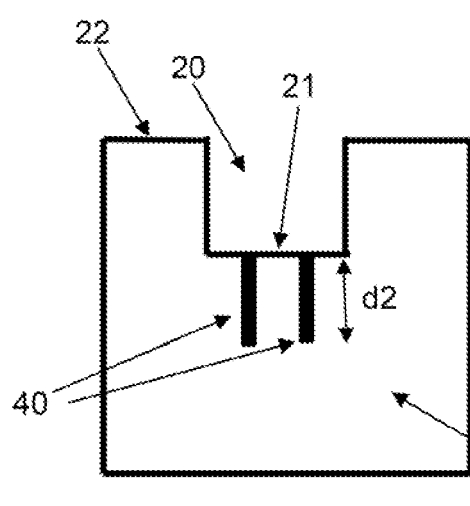
FIG. 5 illustrates a sectional view of a wound following a fractional laser ablation process according to one embodiment described herein.
Figure 6:
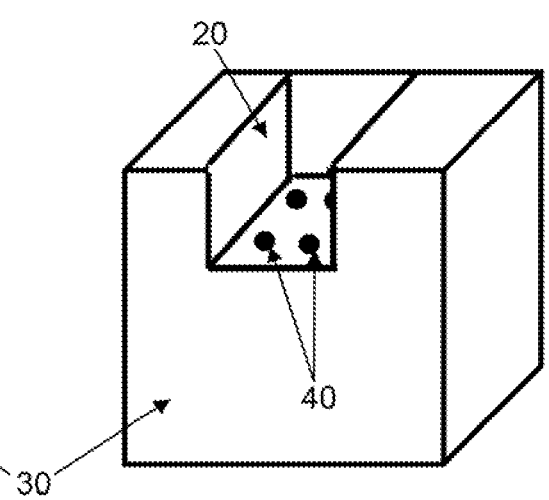
FIG. 6 illustrates a perspective view of the wound of FIG. 5.

An exemplary fractional laser ablation process is illustrated in FIG. 5 and FIG. 6. In particular, FIG. 5 and FIG. 6 schematically illustrate the results of a fractional laser ablation step carried out in a wound bed (20) of a host (30) following the field laser ablation step illustrated in FIGS. 1-4. As illustrated in FIG. 5 and FIG. 6, a fractional laser ablation beam (not shown) forms columnar vacancies or holes (40) having a depth (d2) below the exterior surface (21) of the wound bed (20). As specifically illustrated in FIG. 5 and FIG. 6, the ablating laser beam forms a 2×2 array of holes (40) in the wound bed (20). However, this particular array is shown for illustration purposes only; it is to be understood that any desired number or pattern of holes (40) can be provided by a fractional laser ablation step described herein. It should further be noted that FIG. 5 illustrates a sectional view of the wound bed (20), while FIG. 6 illustrates a perspective view of the same wound bed (20) after completion of the fractional laser ablation to depth d2.

The depth and areal density of ablation in a fractional laser ablation step described herein can vary. Any depth and areal density not inconsistent with the objectives of the present disclosure may be used. For example, in some preferred embodiments, the fractional laser ablation generates holes in up to 25% or up to 35% of the surface area of the wound bed, the holes having an average diameter of 150-600 µm and an average depth of up to 2 mm. In other cases, the fractional laser ablation generates holes in 15-35%, 15-30%, 15-25%, 20-35%, or 20-30% of the surface area of the wound bed, wherein the holes have an average diameter of 150-500 µm, 150-450 µm, 150-400 µm, 200-600 µm, 200-500 µm, 200-450 µm, 200-400 µm, 250-600 µm, 250-500 µm, 250-450 µm, 250-400 µm, 300-600 µm, 300-500 µm, 300-450 µm, 300-400 µm, 400-600 µm, 400-500 µm, or 450-600 µm, and a depth of 0.3-2.5 mm, 0.3-2 mm, 0.3-1.5 mm, 0.3-1 mm, 0.5-2.5 mm, 0.5-2 mm, 0.5-1.5 mm, 0.5-1 mm, 1-2.5 mm, or 1-2 mm.

The spot size of a fractional laser ablation may also vary. Any spot size not inconsistent with the objectives of the present disclosure may be used. In some cases, for instance, the spot size is 0.1-1 mm or 0.1-0.5 mm.

Moreover, a laser or laser beam used for a fractional laser ablation step described herein can have any power and any peak or average emission wavelength not inconsistent with the objectives of the present disclosure. For example, in some embodiments, a laser or laser beam used for fractional laser ablation has a peak or average emission wavelength in the IR region of the electromagnetic spectrum. In some such cases, a laser or laser beam used for fractional laser ablation has a peak or average emission wavelength in the range of 1-4 µm, 1-3 µm, 2-4 µm, 2-3 µm, 8-12 µm, or 9-11 µm. For example, in some embodiments, the fractional laser ablation is preferably carried out using an Er:YAG laser or laser beam. In other cases, the fractional laser ablation is carried out using a carbon dioxide laser or laser beam. Further, in some instances, a laser or laser beam used for fractional laser ablation or coagulation has an average power of 1 to 100 W.

Additionally, in some preferred embodiments, a fractional laser ablation is carried out using a laser scanner. Such a "laser scanner" refers to an apparatus similar to or the same as that described above in the context of full field laser ablation. In addition, a fractional scanner may have elements which either deliver a single small beam to a portion of the area of interest or an array of multiple small spots which can be directed as a pattern to interact with a fraction of the area of interest. Such a fractional scanner may be similar to the full field scanner with additional optical components, removed, added or adjusted accordingly.

It is further to be understood that a fractional laser ablation step described herein can be carried out using any laser system not inconsistent with the objectives of the present disclosure. Such a system may, for instance, include a laser operable to produce a laser beam having characteristics described hereinabove for fractional laser ablation, as well as one or more lenses, mirrors, actuators, or other hardware or software for directing the laser beam to a desired location on a patient and/or within a wound bed. One exemplary system is described further hereinbelow in Section II.

Not intending to be bound by theory, it is believed that carrying out a fractional laser ablation step described herein can stimulate host immune responses or other wound-healing responses of the host, such as responses leading to angiogenesis, host ECM formation, reduction of inflammation, reduction in cellular senescence in the wound bed, and/or improved number and/or penetration of host neutrophils, other white blood cells, cytokines, and/or growth factors into the wound bed from deeper, healthier host tissue.

Moreover, in some embodiment's, the fractional laser ablation of a method described herein is begun at essentially "the same time" as the full field laser ablation is ended, and the two treatment modalities are delivered sequentially, from a clinical perspective. For instance, in some cases, the fractional laser ablation is begun 1 hour or less, 30 minutes or less, 20 minutes or less, 15 minutes or less, 10 minutes or less, 5 minutes or less, 3 minutes or less, or 1 minute or less after the full field laser ablation is ended. It is also possible, in some cases, for the fractional laser ablation to be carried out simultaneously or nearly simultaneously with the full field laser ablation, or partially temporally overlapping the full field laser ablation. For example, in some embodiments, a laser described herein has a beam shape that simultaneously contains the properties necessary (e.g., peak power, number of spots, spot size, spot location) to treat a wound bed in both a full field and a fractional manner in the same laser firing. In other cases, a laser scanner is controlled or configured to switch rapidly between two optical configurations, namely, a full field mode and a fractional mode during the scan itself. In still other instances, fractional ablation is begun in the wound bed (e.g., in a first region or location within the wound bed) while full field ablation is finishing elsewhere (e.g., in a second region or location within the wound bed). Moreover, in some embodiments, any blood that enters the wound bed after or due to full field ablation is removed prior to beginning fractional laser ablation. For instance, in some cases, any such blood is removed by blotting or wiping in between performing full field laser ablation and fractional laser ablution in a given location or region within the wound bed.

Methods described herein, in some, embodiments, further comprise performing debridement in the wound bed, including prior to performing full field laser ablation in the wound bed. Moreover, in some cases, performing debridement produces punctate bleeding in the wound bed. Performing debridement can prepare the wound bed for subsequent steps of a method described herein. Moreover, such a debridement "pre-treatment" can be used to remove substantial amounts of callous dead tissue from the wound bed, particularly at the wound edge.

For instance, in some cases, debridement can remove up to 2 mm or up to 3 mm of tissue, where the recited length corresponds to a depth from the surface of the wound or wound bed prior to debridement. In some embodiments, the debridement step removes 0.5-3 mm, 0.5-2.5 mm, 0.5-2 mm, 1-3 mm, 1-2.5 mm, 1-2 mm, or 2-3 mm of tissue from the wound bed.

Debridement can be performed in any manner not inconsistent with the objectives of the present disclosure. For example, in some cases, performing debridement comprises performing sharp debridement. Alternatively, in other instances, performing debridement comprises performing laser debridement. It is to be understood that such laser debridement as a "pre-treatment" debridement step can differ from other laser treatment steps of methods described herein. In particular, such laser debridement differs from full field laser ablation and fractional laser ablation steps described herein.

It is further to be understood that, in some cases, debridement can be entirely omitted from a method described herein. In some embodiments, for example, less severe wounds may be treated by eliminating or omitting a debridement step such as a sharp debridement step and can instead use a full field laser ablation step, such as described above, to sufficiently prepare the otherwise untreated wound bed for fractional laser ablation. In some such instances, the full field laser ablation can be carried out using a scan depth and desired number of "passes" of the full field laser as is necessary to remove tissue to the point of punctate bleeding.

As stated above, it is believed that methods described herein can dramatically improve wound healing, especially chronic wound healing, by hindering or destroying the ability of biofilm present in a wound bed from reforming and/or otherwise limiting the effectiveness of antibiotic treatments, other treatments, and host immune responses to the wound. Thus, in some embodiments, a method described herein can "reset" the wound microbiota and the wound bed surface. Again not intending to be bound by theory, it is believed that a method described herein can provide this benefit in a number of ways. For instance, in some cases, the method removes at least 85% of biofilm or residual biofilm present in the wound bed prior to performing the full field laser ablation. In some instances, the method removes at least 90%, at least 95%, or at least 98% of biofilm or residual biofilm in the wound bed immediately prior to performing the full field laser ablation.

Moreover, methods described herein, in some cases, further comprise carrying out one or more additional treatments in the wound bed following debridement, full field laser ablation, and/or fractional laser ablation steps. Any such additional treatments not inconsistent with the objectives of the present disclosure can be used. For example, in some instances, an additional treatment includes applying an antibiotic to the wound, desiccating the wound, and/or irradiating the wound with UV light. As described further herein, it is believed that performing full field and fractional laser ablation steps described herein can not only enable the host to self-heal a treated wound, but can also increase the efficacy of traditional, non-laser ablation wound treatments, such as antibiotic treatments.

Additionally, as stated above, it should be further noted that methods described herein can also be used to treat damaged tissue that may or may not constitute a "wound" per se. For example, in some cases, a method described herein comprises treating a damaged tissue site other than a wound by performing a full field laser ablation in, at, or on a non-wound damaged tissue site and subsequently performing a fractional laser ablation in, at, or on the non-wound damaged tissue site. In such instances, it is further to be understood that any of the steps described above for treating a wound can be performed in the same way or substantially the same way for treating a non-wound damaged tissue site.

Moreover, it is further to be understood that a method described herein can include any combination of steps or other features described above not inconsistent with the objectives of the present disclosure. For example, any debridement step described herein can be combined with any full field or fractional laser ablation step and/or laser feature described herein. Similarly, a method described herein can be carried out with any system or device described herein.

II. Systems or Devices for Treating a Wound

In another aspect, systems or devices for treating a wound (or other damaged tissue site) are described herein. It is to be understood that such systems or devices can be used to carry out a method described hereinabove in Section I. In some cases, such a system or device comprises a laser configured to selectively perform full field laser ablation and fractional laser ablation on a wound (or other damaged tissue site) of the same patient, including in an alternating or sequential manner. In some such instances, the laser is configured to perform fractional laser ablation on the wound (or other damaged tissue site) after the laser performs full field laser ablation on the wound (or other damaged tissue site). Moreover, in some cases, a system or device described herein comprises a plurality of lasers rather than a single laser. For instance, in some embodiments, a system or device comprises a first laser configured to perform full field laser ablation, and a second laser configured to perform fractional laser ablation. Additionally, in some embodiments, the system or device further comprises one or more first lenses, mirrors, actuators, or other hardware or software for directing a first laser beam generated by a laser of the system or device (such as by a first laser) to a desired location on a patient and/or within a wound bed (or non-wound damaged tissue site). The system or device may also comprise one or more second lenses, mirrors, actuators, or other hardware or software for directing a second laser beam generated by a laser of the system or device (such as by the same laser used to generate the first laser beam, or by a second laser) to a desired location on a patient and/or within a wound bed (or non-wound damaged tissue site). Moreover, in some instances, a system or device described herein further comprises hardware and/or software for coordinating or automating the operation of one or more lasers of the system or device (such as first and second lasers), including to provide a plurality of laser beams (such as first and second laser beams) in a simultaneous or sequential manner described herein.

In some eases, a laser or plurality of lasers (e.g., the first laser and the second laser) of a system or device described herein perform full field laser ablation and fractional laser ablation on a wound of the same patient sequentially. In some such instances, for example, a laser (or a second laser) performs fractional laser ablation on the wound after the same laser (or a first laser) performs full field laser ablation on the wound. It is also possible, in some cases, for the fractional laser ablation to be carried out simultaneously or nearly simultaneously with the field laser ablation, or partially temporally overlapping the full field laser ablation, as described above in Section I.

Figure 7:
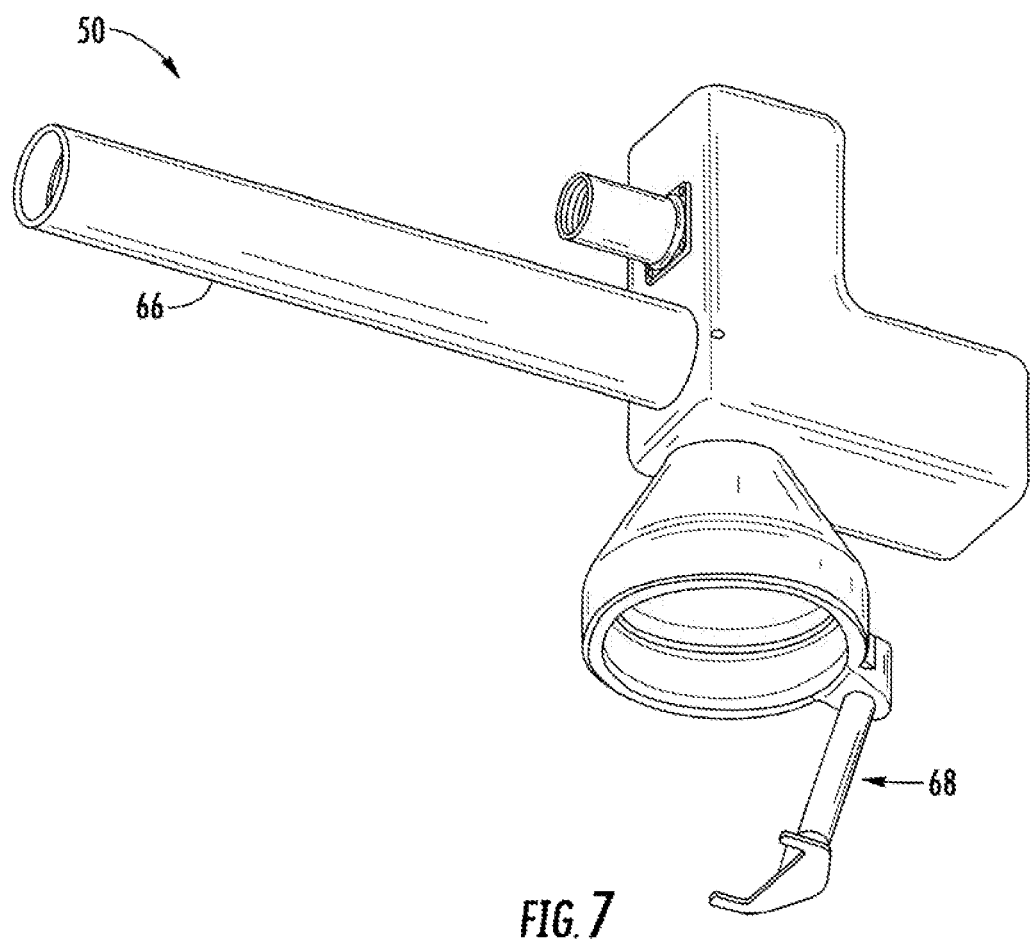
FIG. 7 illustrates a perspective view of a laser treatment device according to one embodiment described herein.
Figure 8:
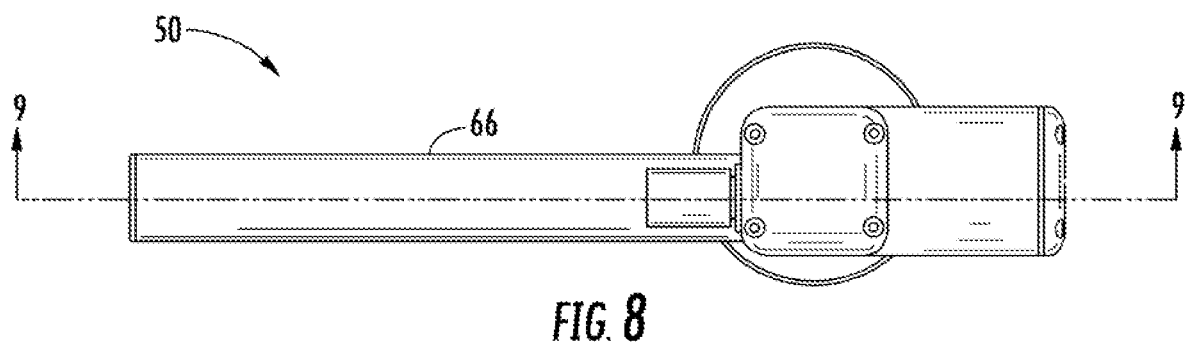
FIG. 8 illustrates a plan view of the device of FIG. 7.
Figure 9:
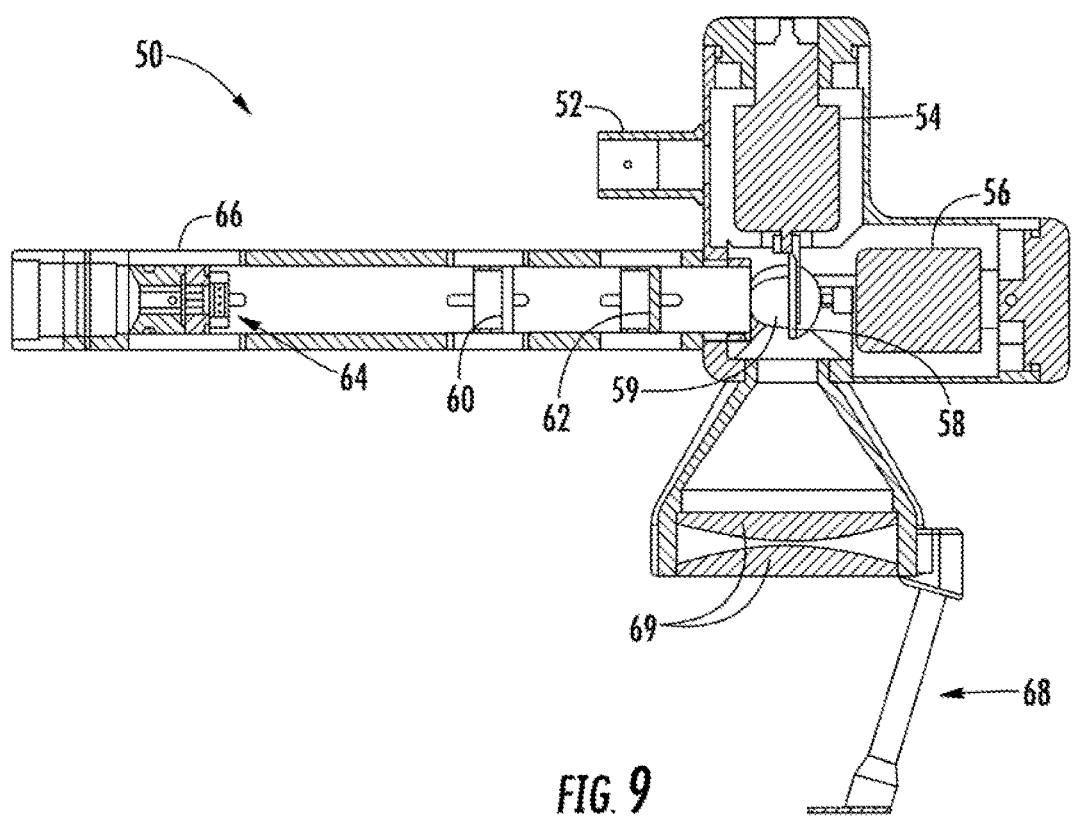
FIG. 9 illustrates a sectional view of the device of FIG. 8, taken along lines 9-9.

One exemplary device, generally designated 50, according to the present disclosure is illustrated schematically in FIGS. 7-9. FIG. 7 illustrates an external asymmetric view of a "combination" full field and fractional scanning handpiece device. FIG. 8 shows a top view of the combination scanning handpiece device. FIG. 9 illustrates a sectional view of the device of FIG. 8, taken along the elongated axis of the tube 66 as viewed along lines 9-9. With specific reference to FIG. 9, both the full field scanner and the fractional scanner employ common elements consisting of the electrical connector 52, x-galvo 54, y-galvo 56, x-mirror 58, y-mirror 59 and focusing lens 60. In a fractional scenario, the moveable lens 62 can be moved out of the active optical path to create a fractionated beam array at the wound. A full field large beam can be achieved in at least two ways. In the first scenario, both the Fly's eye assembly 64 and the movable lens 62 can be removed from the active beam path resulting in a full field (non-fractionated) beam. In a second full field scenario, both the Fly's eye assembly 64 and the moveable lens 62 are left in the beam path. Additionally, the focusing lens 60 and moveable lens 62 can be readjusted along the axis of the tube 66 to determine the proper beam parameters for the two scanning modes, fractional and full field. The bayonet standoff 68 insures a desired distance from the scanning handpiece to the area targeted air ablation. One or more fixed lenses 69 can be disposed proximate the bayonet standoff 68 and spaced apart from the area targeted for ablation.

Figure 10:
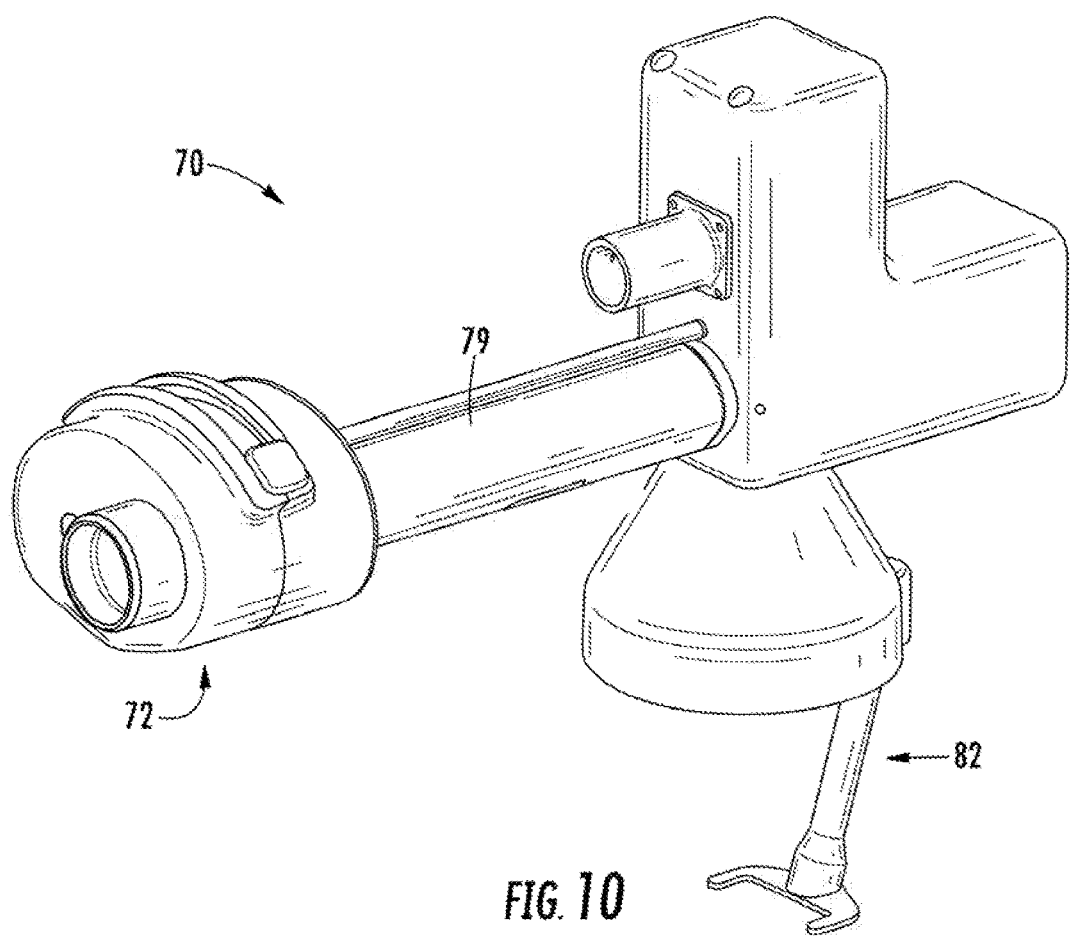
FIG. 10 illustrates a perspective view of as laser treatment device according to one embodiment described herein.
Figure 11:
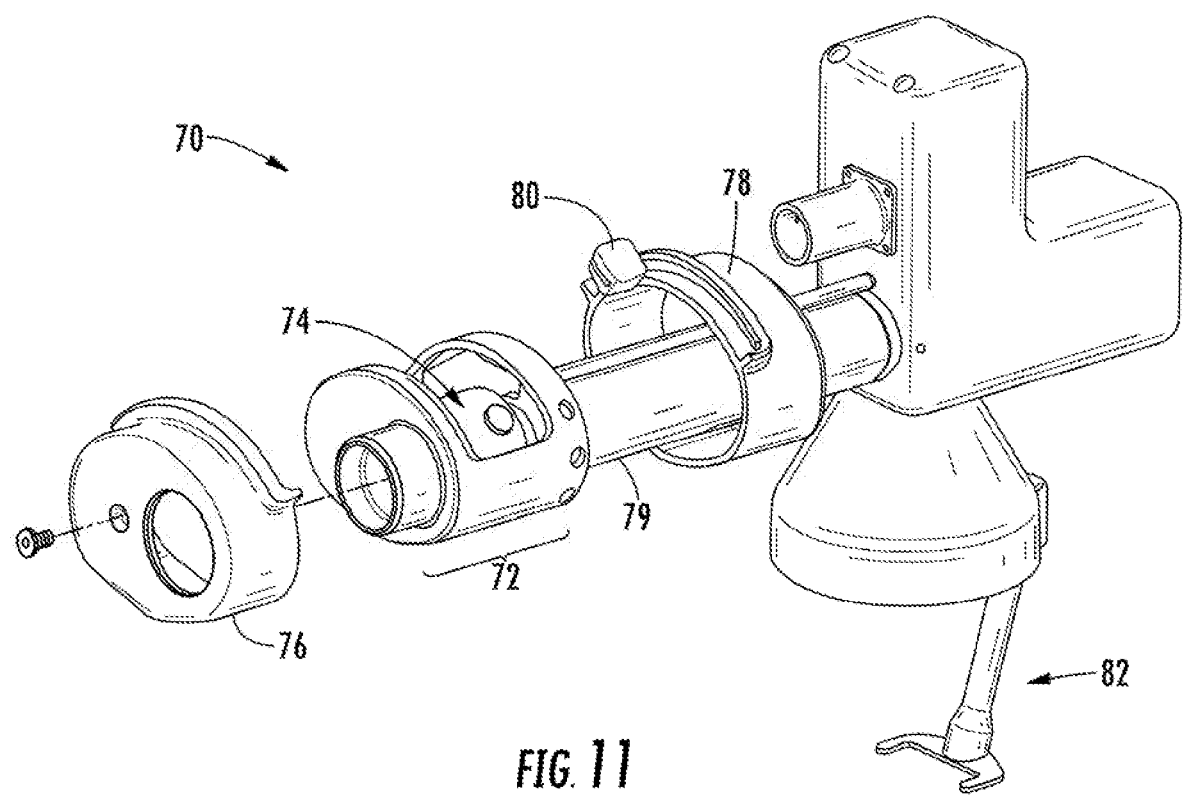
FIG. 11 illustrates a partially exploded view of the device of FIG. 10.

A further exemplary device, generally designated 70, is illustrated in FIGS. 10-11. With specific reference to FIG. 11, the device 70 comprises a lens housing 72 configured to house a movable assembly 74 therein. The assembly 74 can comprise a movable lens and a Fly's eye lens, which are individually or simultaneously movable relative to an optical path formed inside the tube 79. The housing 72 and assembly 74 can be at least partially sealed between a front cover 76 and a rear cover 78. The assembly 74, or portions thereof, can be positionable or out of the active optical path using an actuator 80. In a fractional scenario, either the moveable lens or the Fly's eye lens of the movable assembly 74 can be moved out of the active optical path to create a fractionated beam array at the wound. In another full field scenario, a full field large beam can be achieved via actuating the moveable lens and the Fly's eye lens of the assembly 74 out of the active beam path resulting in a full field (non-fractionated) beam. Alternatively, both the moveable and Fly's eye lenses of the assembly 74 can be left in the beam path. The bayonet standoff 82 insures a desired distance from the scanning handpiece device 70 to the area targeted for ablation.

Turning now to specific components of systems or devices described herein, a system or device described herein comprises one or more lasers, such as a first laser and a second laser. It is to be understood that a "laser" can refer to a single device that produces a single beam of laser light from a single lasing medium. Any laser not inconsistent with the objectives of the present disclosure may be used for the first laser and/or the second laser. In particular, any laser described hereinabove in Section I may be used. For example, in some preferred embodiments, a laser (such as the first laser and/or the second laser) comprises a laser scanner. Additionally, in some preferred embodiments, a laser (such as the first laser and/or the second laser) comprises an Er:YAG laser.

A system or device described herein, in some embodiments, further comprises one or more lenses, mirrors, actuators, or other hardware or software for directing one or more laser beams to a desired location. Any lenses, mirrors, actuators, or other hardware or software not inconsistent with the objectives of the present disclosure may be used. Many suitable lenses, mirrors, actuators, or other hardware or software will be readily apparent to those of ordinary skill in the art.

Moreover, in some instances, a system or device described herein further comprises hardware and/or software for coordinating or automating the operation of one or more lasers of the system or device (such as first and second lasers of a system described herein). Any such hardware and/or software not inconsistent with the objectives of the present disclosure may be used. Moreover, various suitable hardware and software components will be readily apparent to those of ordinary skill in the art.

Additionally, it is to be understood that a system or device described herein can include any combination of components or features described above. For example, any laser (or combination of lasers) described above can be used in combination with any additional hardware and/or software described herein.

Some embodiments described herein are further illustrated in the following non-limiting examples.

Example 1

Method of Treating a Chronic Wound

A method of treating a chronic wound according to one embodiment described herein was carried out as follows. The patient was a very pleasant 50-year-old diabetic with severe peripheral neuropathy and peripheral vascular disease. The patient had had a right below knee amputation. The patient developed a severe Wagner's III diabetic foot ulcer of the left lateral foot in September 2015. The patient underwent biofilm based wound management and, on Oct. 23, 2015, the patient continued to have a deep diabetic foot ulcer which involved the metatarsal of the left lateral foot. The patient was started on laser ablation treatments as described herein in Section I. Within one month the wound had filled in, covering the bone, and was almost up to the wound surface. By Dec. 23, 2015, the patient's wound was healed. Prior to the beginning of treatment according to a method described herein, the patient was recommended to have his left leg amputated. Such amputation was not needed due to the efficacy of the wound treatment described herein.

Example 2

Method of Treating a Chronic Wound

A method of treating a chronic wound according to one embodiment described herein was carried out as follows. The patient was a very pleasant 59-year-old male with severe diabetes mellitus which is uncontrolled. The patient developed a Wagner's IV diabetic foot ulcer of the left lower leg. The patient had involvement of the calcaneus and the Achilles tendon and was recommended to have a major limb amputation, either above knee, or at the very minimum, below knee. The patient wanted to try conservative management first. On Dec. 14, 2015, there was involvement of the calcaneus and the Achilles tendon along with significant loss of skin of the calf and significant slough and maceration on and around the peri wound area. The patient was started with laser ablation treatment as described hereinabove in Section I laser management and has had 5 treatments to date. By roughly three weeks after initiation of treatment, the maceration was gone, the wound bed had markedly improved and there was reepithelialization across the calf region. By Feb. 1, 2016, most of the defect deep around the calcaneus had healed. There had been reepithelialization of over 80% of the wound. There was still slough formation in the calcaneal region but clear evidence of healing. It was clear that this wound would heal and the patient would not lose his limb.

Additional exemplary embodiments contemplated herein are as follows:

Embodiment 1: A method of treating a wound, the method comprising:
performing a full field laser ablation in a wound bed of the wound; and
subsequently performing a fractional laser ablation in the wound bed.

Embodiment 2: The method of Embodiment 1, wherein the fractional laser ablation is begun 10 minutes or less after the full field laser ablation is ended.

Embodiment 3: The method of any of the preceding Embodiments, wherein the full field laser ablation removes at least 90% of biofilm and/or necrotic tissue present in the wound bed immediately prior to the full field laser ablation.

Embodiment 4: The method of any of the preceding Embodiments, wherein the fractional laser ablation generates holes in up to 35% of the surface area of the wound bed, the boles having an average diameter of 150-600 μm and an average depth of up to 2 mm.

Embodiment 5: The method of any of the preceding Embodiments, wherein the full field laser ablation and/or the fractional laser ablation is carried out using a laser scanner.

Embodiment 6: The method of Embodiment 5, wherein both the full field laser ablation and the fractional laser ablation are carried out using a laser scanner.

Embodiment 7: The method of any of the preceding embodiments, wherein the full field laser ablation and/or the fractional laser ablation is carried out using san Er:YAG laser.

Embodiment 8: The method of Embodiment 7, wherein both the full field laser ablation and the fractional laser ablation are carried out using an Er:YAG laser.

Embodiment 9: The method of any of the preceding Embodiments further comprising performing debridement in the wound bed prior to performing the full field laser ablation in the wound bed.

Embodiment 10: The method of Embodiment 9, wherein performing debridement produces punctate bleeding in the wound bed.

Embodiment 11: The method of Embodiment 9, wherein performing debridement comprises performing sharp debridement.

Embodiment 12: The method of Embodiment 9, wherein performing debridement comprises performing laser debridement.

Embodiment 13: The method of any of the preceding Embodiments, wherein the method removes at least 85% of biofilm or residual biofilm present in the wound bed prior to performing the full field laser ablation.

Embodiment 14: The method of any of the preceding Embodiments, wherein the wound is a chronic wound.

Embodiment 15: A device for treating a wound, the device comprising:
a laser configured to perform full field laser ablation and fractional laser ablation.

Embodiment 16: The device of Embodiment 15, wherein the laser performs full field laser ablation and fractional laser ablation on a wound of the same patient sequentially.

Embodiment 17: The device of Embodiment 16, wherein the laser performs fractional laser ablation on the wound after the laser performs full field laser ablation on the wound.

Embodiment 18: The device of any of the preceding Embodiments, wherein the laser comprises a laser scanner.

Embodiment 19: The device of any of the preceding Embodiments, wherein the laser comprises an Er:YAG laser.

Embodiment 20: The device of any of the preceding Embodiments, wherein the device further comprises one or more lenses, mirrors, and/or actuators for directing one or more laser beams produced by the laser to one or more desired locations on a patient having the wound and/or within a wound bed of the wound.

Various embodiments of the present invention have been described in fulfillment of the various objectives of the invention. It should be recognized that these embodiments are merely illustrative of the principles of the present invention. Numerous modifications and adaptations thereof will be readily apparent to those skilled in the art without departing from the spirit and scope of the invention.

The invention claimed is:

1. A method of treating a wound the method comprising:
performing a full field laser ablation in a wound bed of the wound; and
subsequently performing a fractional laser ablation in the wound bed,
wherein full field laser ablation is laser ablation in which laser interaction with tissue corresponds to at least 90% of the wound bed with an ablating laser beam,
wherein an "ablating" laser beam is a laser beam of sufficient peak power to ablate, vaporize, destroy, and/or remove biological tissue irradiated by the laser beam, and
wherein fractional laser ablation is laser ablation or coagulation in which an ablating or coagulating laser beam selectively ablates, coagulates, vaporizes, destroys, or removes columns of tissue, or "drills holes," in a wound bed.

2. The method of claim 1, wherein the fractional laser ablation is begun 10 minutes or less after the full field laser ablation is ended.

3. The method of claim 1, wherein the full field laser ablation removes at least 90% of biofilm and/or necrotic tissue present in the wound bed immediately prior to the full field laser ablation being performed.

4. The method of claim 1, wherein the fractional laser ablation generates holes in up to 35% of the surface area of the wound bed, the holes having an average diameter of 150-600 μm, and an average depth of up to 2 mm.

5. The method of claim 1, wherein the full field laser ablation and/or the fractional laser ablation is carried out using a laser scanner.

6. The method of claim 5, wherein both the full field laser ablation and the fractional laser ablation are carried out using a laser scanner.

7. The method of claim 1, wherein at least one of the full field laser ablation and the fractional laser ablation is carried out using an Hr:YAG laser.

8. The method of claim 7, wherein both the full field laser ablation and the fractional laser ablation are carried out using an Kr:YAG laser.

9. The method of claim 1, further comprising performing debridement in the wound bed prior to performing the full field laser ablation in the wound bed.

10. The method of claim 9, wherein performing debridement produces punctate bleeding in the wound bed.

11. The method of claim 9, wherein performing debridement comprises performing sharp debridement.

12. The method of claim 9, wherein performing debridement comprises performing laser debridement.

13. The method of claim 1, wherein the method removes at least 85% of biotilm or residual biofilm present in the wound bed prior to performing the full field laser ablation.

14. The method of claim 1, wherein the wound is a chronic wound.

15. A device for treating a wound, the device comprising:

a laser configured to selectively perform full field laser ablation and fractional laser ablation, wherein full field laser ablation is laser ablation in which laser interaction with tissue corresponds to at least 90% of the wound bed with an ablating laser beam, wherein an "ablating" laser beam is a laser beam of sufficient peak power to ablate, vaporize, destroy, and/or remove biological tissue irradiated by the laser beam, and wherein fractional laser ablation is laser ablation or coagulation in which an ablating or coagulating laser beam selectively ablates, coagulates, vaporizes, destroys, or removes columns of tissue, or "drills holes," in a wound bed.

16. The device of claim 15, wherein the laser performs full field laser ablation and fractional laser ablation on a wound of the same patient sequentially.

17. The device of claim 16, wherein the laser performs fractional laser ablation on the wound after the laser performs full field laser ablation on the wound.

18. The device of claim 15, wherein the laser comprises a laser scanner.

19. The device of claim 15, wherein the laser comprises an Er:YAG laser.

20. The device of claim 15, wherein the device further comprises one or more lenses, mirrors, and/or actuators for directing one or more laser beams produced by the laser to one or more desired locations on a patient having the wound and/or within a wound bed of the wound.

* * * * *